United States Patent
Park et al.

(10) Patent No.: US 8,492,157 B2
(45) Date of Patent: Jul. 23, 2013

(54) MICROFLUIDIC DEVICE AND HEMOGLOBIN MEASUREMENT METHOD USING THE SAME

(75) Inventors: Jong Myeon Park, Incheon-si (KR); Won Yong Lee, Yongsan-gu (KR); Han Nim Choi, Seoul (KR); Jung Hoon Lee, Jinju-si (KR)

(73) Assignees: Samsung Electronics Co., Ltd., Suwon-si (KR); Industry-Academic Cooperation Foundation, Yonsei University, Seoul (KR)

(*) Notice: Subject to any disclaimer, the term of this patent is extended or adjusted under 35 U.S.C. 154(b) by 69 days.

(21) Appl. No.: 13/294,860

(22) Filed: Nov. 11, 2011

(65) Prior Publication Data

US 2012/0122139 A1    May 17, 2012

(51) Int. Cl.
*G01N 33/72* (2006.01)
*G01N 33/48* (2006.01)
*G01N 1/18* (2006.01)
*G01N 21/76* (2006.01)
*C12Q 1/02* (2006.01)
*C12M 1/34* (2006.01)

(52) U.S. Cl.
USPC ............ 436/66; 436/45; 436/63; 436/67; 436/164; 436/165; 436/166; 436/172; 436/177; 436/180; 422/64; 422/68.1; 422/82.08; 422/502; 422/503; 422/504; 422/506; 422/533; 422/537; 422/548; 422/551; 422/552; 422/559; 435/29; 435/288.7; 435/287.3; 435/288.4; 435/288.5

(58) Field of Classification Search
USPC .............. 436/43, 45, 63, 66, 67, 164, 165, 436/166, 172, 174, 177, 180; 422/408, 415, 422/417, 430, 63, 64, 68.1, 81, 82.05, 82.08, 422/501, 502, 503, 504, 506, 507, 533, 537, 422/547, 548, 551, 552, 554, 559; 435/29, 435/288.7, 287.3, 288.4, 288.5
See application file for complete search history.

(56) References Cited

U.S. PATENT DOCUMENTS

| | | | | |
|---|---|---|---|---|
| 4,861,728 | A * | 8/1989 | Wagner | 436/501 |
| 5,478,754 | A * | 12/1995 | Brandt et al. | 436/518 |
| 6,162,645 | A * | 12/2000 | Lee et al. | 436/67 |
| 6,399,293 | B1 * | 6/2002 | Pachl et al. | 435/4 |
| 6,632,399 | B1 * | 10/2003 | Kellogg et al. | 422/72 |
| 2011/0070658 | A1 * | 3/2011 | Rutter et al. | 436/501 |
| 2011/0143364 | A1 * | 6/2011 | Kim et al. | 435/7.1 |

* cited by examiner

*Primary Examiner* — Maureen Wallenhorst
(74) *Attorney, Agent, or Firm* — Sughrue Mion, PLLC

(57) ABSTRACT

A microfluidic device and a method for measurement of biomaterials using the same. The microfluidic device includes a microfluidic structure including: a sample chamber which receives and accommodates blood; a reagent chamber which contains a luminescent reactant; a first detection chamber which contains a first material that is positively charged; a second detection chamber which is connected to the first detection chamber, and contains a second material having a boronate moiety; and at least one channel which connects the sample chamber, the reagent chamber and the first and second detection chambers.

20 Claims, 6 Drawing Sheets

MICROFLUIDIC DEVICE AND HEMOGLOBIN MEASUREMENT METHOD USING THE SAME

CROSS-REFERENCE TO RELATED APPLICATION

This application claims priority from Korean Patent Application No. 10-2010-0112405, filed Nov. 12, 2010 in the Korean Intellectual Property Office, the disclosure of which is incorporated herein by reference.

BACKGROUND

1. Field

Apparatuses and methods consistent with exemplary embodiments relate to a microfluidic device and a method of measuring biomaterials using the same and, more particularly, to a microfluidic device for measuring hemoglobin based upon chemical luminescence and a method of measuring hemoglobin using the same.

2. Description of the Related Art

A microfluidic device generally refers to a device used for conducting biological or chemical reactions using a small amount of fluid.

In general, a microfluidic structure of a microfluidic device, which has at least one independent function, includes a chamber containing a fluid therein, a channel through which the fluid flows and a valve for controlling the fluid flow, and the microfluidic structure may be fabricated by different combinations of these components. In particular, a device having a microfluidic structure mounted on a substrate in a chip form such that procedures involving biological or chemical reactions can be conducted on a small chip, in order to execute several testing processes and/or operations on the structure, is referred to as a "Lab-on-a chip." In order to move a fluid within the microfluidic structure, a driving pressure is generally required. The driving pressure may be capillary pressure or pressure generated using an additional pump may be employed. For example, a disc-type microfluidic device having a microfluidic structure mounted on a disc-type rotational platform and using centrifugal force to move a fluid in order to execute a series of tasks has been proposed.

Since glycated hemoglobin (Hemoglobin A1c; hereinafter, sometimes referred to as 'HbA1c') has recently been recognized to have an important role in selection and diagnosis of diabetes mellitus, the necessity thereof in outpatient testing and emergency outpatient testing for new patients has been increased.

Outpatient testing and/or emergency outpatient testing must be completed within 30 minutes from starting to reporting and, according to a result thereof, instruction of a further stage is determined. Therefore, a rapid test method and accurate results are required.

However, related art techniques for measurement of glycated hemoglobin may have problems such as a long period of time for measurement, difficulties in handling or management, or the like. Accordingly, there is a need for a method of performing measurement with improved speed and accuracy capable of overcoming such technical limitations.

SUMMARY

Exemplary embodiments provide a microfluidic device capable of detecting hemoglobin containing a transition metal, Fe, which functions as a catalyst for chemical luminescence reaction, as well as glycated hemoglobin, by chemical luminescence detection, and a method of measuring glycated hemoglobin using the foregoing device.

According to an aspect of an exemplary embodiment, there is provided a microfluidic structure including: a sample chamber which receives and accommodates blood; a reagent chamber which contains a luminescent reactant; a first detection chamber which contains a first material that is positively charged; a second detection chamber which is connected to the first detection chamber, and contains a second material having a boronate moiety; and at least one channel which connects the sample chamber, the reagent chamber and the first and second detection chambers.

The luminescent reactant may include a luminescent material and an oxidant.

The luminescent material may be at least one selected from a group consisting of luminol, ucigenin, 7-(4,6-dichloro-1,3, 5-triazinylamino)-4-methylcoumarin) (DTMC), pyrene, perylene, p-quarterphenyl, 1,6-diphenyl-1,3,5-hexatriene, 1,3-cyclohexanedione, 1,4-bis(5-phenyloxazol)benzene, bis (2,4-dimethylpentadienyl)ruthenium, 1-ethylnaphthalene, 1-pyrenedodecanoic acid, 2,3-naphthalenedicarboxaldehyde, 2-aminoacridone, 3-phenylumbelliferone, 3,3'-diethylthiadicarbocyanine iodide, 4-hydroxybenzhydrazide, 6-aminofluorescein, 7-ethoxy-4-methylcoumarin and 7-methoxycoumarin.

The first material in the first detection chamber may have an amine group or a polyamine group.

The first detection chamber may have a fixing region to which the first material is fixed.

The boronate moiety may be selected from a group consisting of boric acid, boronate compounds and phenylboronic acid.

The second detection chamber may have a fixing region to which the second material containing the boronate moiety is fixed.

The fixing region in the detection chamber may be formed using a silicon wafer, glass, quartz, metal or a plastic material.

The fixing region in the detection chamber may include gold, silver, platinum, aluminum and/or copper.

Fluid transportation between the chambers may be controlled by valves.

Each of the valves may be formed using a mixture of a phase transition material and a heating fluid.

The phase transition material may be at least one selected from a group consisting of wax, gel and thermoplastic resin.

The heating fluid may contain a carrier oil and a number of micro-heating particles dispersed in the carrier oil, and the micro-heating particles may be micro-metal oxide particles.

According to an aspect of another exemplary embodiment, there is provided a microfluidic device including: a platform including the microfluidic structure as set forth above; a detection unit; and an external energy source to supply energy to the valve, wherein a fluid may be transported using centrifugal force generated by rotation of the platform.

The external energy source may be a laser.

The detection unit may detect light generated through chemical luminescence of the luminescent reactant described above.

According to an aspect of another exemplary embodiment, there is provided a method of measuring hemoglobin including: injecting blood into a sample chamber of the microfluidic device; transporting the blood from the sample chamber into a first detection chamber of the microfluidic device and combining hemoglobin contained in the blood with a first material fixed inside the first detection chamber; transporting the blood from the first detection chamber into a second detection chamber and combining glycated hemoglobin contained in the blood with a second material having a boronate moiety fixed inside the second detection chamber; transporting a luminescent reactant received in a reagent chamber of the microfluidic device into the first and second detection chambers to induce chemical luminescence; detecting light generated through chemical luminescence in the first and second detection chambers; and measuring hemoglobin based on the detected light.

The measuring of hemoglobin including includes measuring hemoglobin in the blood based on the detected light generated through chemical luminescence in the first detection chamber and measuring glycated hemoglobin in the blood based on the detected light generated through chemical luminescence in the second detection chamber.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
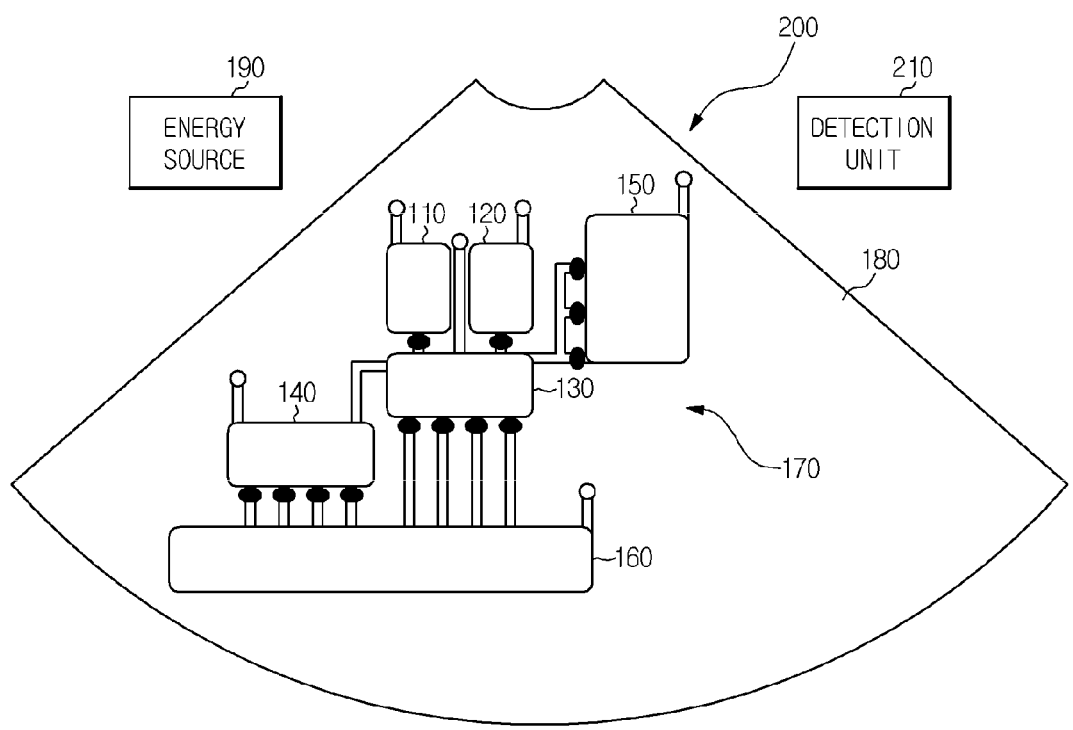
FIG. 1 is a schematic view illustrating the construction of a microfluidic device according to an exemplary embodiment.

Hereinafter, exemplary embodiments will be described with reference to the accompanying drawings. However, the present invention may be embodied in various other forms, which are not particularly restricted to those described herein.

In the accompanying drawings, like reference numerals denote elements substantially having the same configurations or performing similar functions and actions throughout the drawings. Separate structures such as a chamber, a channel, and the like are simply illustrated and dimensional ratios of the same may be different from real scales thereof, instead being enlarged or reduced. In expressions such as 'microfluidic device,' 'micro-particle,' etc., 'micro' is not limitedly construed as a size unit but is used in contrast with 'macro.'

FIG. 1 is a schematic view illustrating the construction of a microfluidic device according to an exemplary embodiment.

As illustrated in FIG. 1, a microfluidic device 200 according to an exemplary embodiment may include at least one microfluidic structure 170 formed in a platform 180. The microfluidic structure 170 includes a plurality of chambers, at least one channel through which the chambers are connected, and at least one valve for opening and closing the channel.

The platform 180 may be a circular disc-type platform 180. However, a shape of the platform 180 is not particularly limited to such circular disc form. The platform 180 may be formed using acryl or other plastic materials, each of which is easily formable and has a biologically inactive surface. However, any materials having chemical or biological stability, optical transparency and/or mechanical workability may be sufficiently used, without being particularly limited thereto. That is, the platform 180 may be fabricated using at least one selected from a variety of materials such as plastic, polymethylmethacrylate (PMMA), glass, mica, silica, a silicon wafer material, plastics, or the like. The plastic material may be selected in view of economic merits and simple workability. Practically available plastic materials may include polypropylene, polyacrylate, polyvinylalcohol, polyethylene, polymethylmethacrylate, polycarbonate, etc.

Also, the platform 180 may include multiple layers of plates. If a depressed intaglio structure corresponding to a chamber or a channel is formed on a side at which two plates face each other and two or more intaglio structures are combined, an empty space and/or channel may be provided inside the platform. Such combination of plates may be achieved using an adhesive or a two-sided adhesive tape, ultrasonic welding, etc.

One or plural microfluidic structures 170 may be provided on the platform 180. For instance, after partitioning the platform 180 into several sections, individual microfluidic structures 170 may be placed independently of one another on the sections, respectively.

The term "microfluidic structure" used herein refers to a general structure which consists of a plurality of chambers, channels and valves and induces a fluid flow, instead of a particular structural substance. Therefore, the microfluidic structure may form a specific unit with different functions or performances according to features in arrangement of chambers, channels and/or valves, and/or kinds of materials received in the structure.

When centrifugal force is used as a driving pressure to transport a fluid, the platform 180 may be a rotatable disc-type platform. However, the platform is not particularly limited to such a disc-type and may adopt a rotatable circular disc shape or a rotatable sector shape that is placed on and fixed to a rotatable frame. In order to turn the platform 180, a rotational driving part may be included to allow high speed rotation of the platform.

The chambers may include a sample chamber 110, a reagent chamber 120, a first detection chamber 130 and a second detection chamber 140.

The sample chamber 110 may provide a space in which a sample in a fluid state, such as blood, is received and contained.

The sample chamber 110 may have a sample inlet (not shown) through which the sample is injected and a sample receiving part (not shown). The receiving part may have an outlet connected to the first detection chamber 130 and a valve may be mounted on the outlet to control flow of the fluid sample. The valve may control the flow of the sample through the channel. The valve may be any one selected from different types of microfluidic valves. For instance, the valve may be a "normally closed valve" which is maintained in a closed state that closes the channel to prevent fluid from flowing unless the valve is opened by external power. A structure for generating capillary pressure which allows the injected sample from the sample inlet to flow toward the sample receiving part by injection pressure while preventing the fluid sample in the sample receiving part from flowing backward to the sample inlet, that is, a capillary valve structure through which the sample passes only when a predetermined pressure is applied, may be provided between the sample inlet and the sample receiving part.

The reagent chamber 120 may contain a reactant performing chemical luminescence.

Chemical luminescence is a reaction that generates an intermediate in an excited state by reaction of reactants A and B and emits light when the intermediate drops to a ground state. This reaction may be represented by Equation 1 below:

[Equation 1]

According to an exemplary embodiment, the reactant may include a luminescent material and an oxidant. The luminescent material may be any one selected from a group consisting of luminol, ucigenin, 7-(4,6-dichloro-1,3,5-triazinylamino)-4-methylcoumarin) (DTMC), pyrene, perylene, p-quarterphenyl, 1,6-diphenyl-1,3,5-hexatriene, 1,3-cyclohexanedione, 1,4-bis(5-phenyloxazol)benzene, bis(2,4-dimethylpentadienyl)ruthenium, 1-ethylnaphthalene, 1-pyrenedodecanoic acid, 2,3-naphthalenedicarboxaldehyde, 2-aminoacridone, 3-phenylumbelliferone, 3,3'-diethylthiadicarbocyanine iodide, 4-hydroxybenzhydrazide, 6-aminofluorescein, 7-ethoxy-4-methylcoumarin and 7-methoxycoumarin.

Light emitted by such luminescent materials through chemical luminescence may have specific wavelengths such as, 364 nm for ucigenin, 450 nm for 7-(4,6-dichloro-1,3,5-thiazinylamino)-4-methylcoumarin (DTMC), 472 nm for pyrene, 490 nm for perylene, 294 nm for p-quaterphenyl, 428 nm for 1,6-diphenyl-1,3,5-hexatriene, 458 nm for 1,3-cyclohexanedione, 358 nm for 1,4-bis(5-phenyloxazol)benzene, 620 nm bis(2,4-dimethylpentadienyl)ruthenium, 337 nm for 1-ethylnaphthalene, 377 nm for 1-pyrenedodecanoic acid, 480 nm for 2,3-naphthalenedicarboxaldehyde, 538 nm for 2-aminoacridone, 472 nm for 3-phenylumbelliferone, 700 nm for 3,3'-diethylthiadicarbocyanine iodide, 425 nm for 4-hydroxybenzhydrazide, 520 nm for 6-aminofluorescein, 377 nm for 7-ethoxy-4-methylcoumarin and 385 nm for 7-methoxycoumarin.

According to an exemplary embodiment, the oxidant may include $H_2O_2$.

For instance, when the luminescent material is luminol and the oxidant is $H_2O_2$, chemical luminescence occurs as follows:

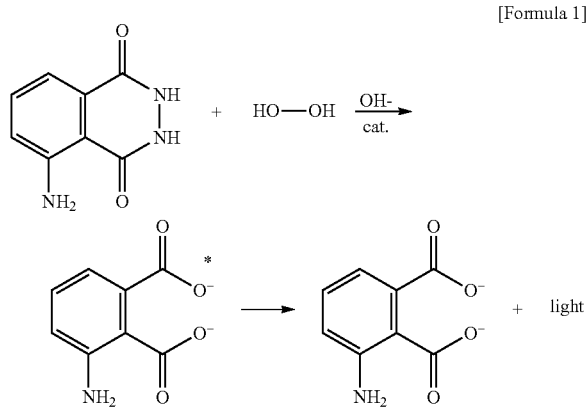
[Formula 1]

The foregoing Formula I shows chemical luminescence of luminol as a luminescent material and $H_2O_2$ as an oxidant. When luminol reacts with $H_2O_2$, it becomes 3-aminophthalate (3-APA) in an excited state. When 3-APA in the excited state drops to a ground state, light at 425 nm is emitted. For chemical luminescence of luminol, a metal ion or metal complex as well as an enzyme may function as a catalyst. According to an exemplary embodiment, a method for chemical luminescence using luminol catalysis of a transition metal, Fe, contained in hemoglobin may be provided.

The reagent chamber 120 is connected to the first detection chamber 130 through a channel and, in order to control flow of the reagent, a valve may be mounted on the channel. The valve may control a flow of the sample through a channel. The valve may be any one of various types of microfluidic valves. For instance, the valve may be a normally closed valve, as described above.

Figure 2:
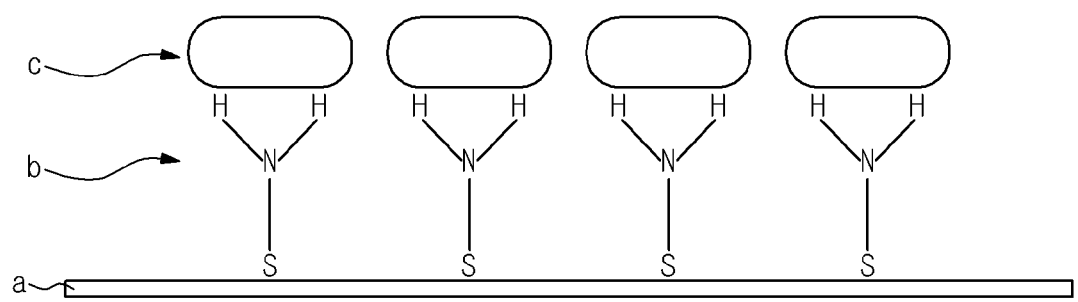
FIG. 2 is a schematic view illustrating a principle of hemoglobin detection in a microfluidic device according to an exemplary embodiment.

The first detection chamber 130 may include a first material (b) non-specifically bonded to hemoglobin (c) and the first material (b) may be a positively charged material and has an amine group or a polyamine group (see FIG. 2).

Figure 3:
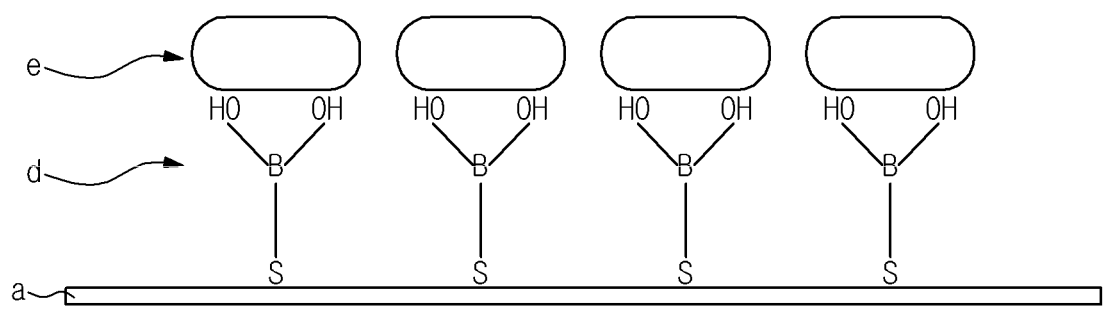
FIG. 3 is a schematic view illustrating a principle of glycated hemoglobin detection in a microfluidic device according to an exemplary embodiment.

The second detection chamber 140 may include a second material (d) specifically bonded to a hydroxyl group of a cis-diol contained in glycated hemoglobin (e). Therefore, the second material (d) bondable to a hydroxyl group of the cis-diol contained in glycated hemoglobin (e) may have a boronate moiety and the boronate moiety may be selected from a group consisting of boric acid, boronate compounds and phenylboronic acid (see FIG. 3).

The second material (d) having the boronate moiety may include, for example, 4-carboxyphenylboronic acid, 3-nitro-5-carboxyphenylboronic acid, m-aminophenylboronic acid, 4-mercaptophenylboronic acid, thiophene-3-boronic acid, phenylboronic acid terminated alkane thiol, etc., without being particularly limited thereto.

The foregoing boronate moiety (HO-B-OH) is bonded to a cis-diol contained in glycated hemoglobin (e), to fix the glycated hemoglobin (e) to the second detection chamber 140.

The glycated hemoglobin is a significant biomolecule in controlling a glucose level in blood of a diabetes mellitus patient, as an accurate index showing an average blood glucose level of a person over the past 2 to 3 months.

A variety of methods for measurement of glycated hemoglobin in blood have been developed. Commercially available methods may include, for example, ion-exchange chromatography, affinity chromatography, electrophoresis, complex colorization, or the like. Such methods are difficult to implement and require skilled technicians to perform complex tasks associated therewith. Also, although an immunological method using an antibody capable of recognizing an N-terminal peptide residue of the glycated hemoglobin to quantify the glycated hemoglobin has been developed, this method has limitations in that the antibody must recognize glycated sites in the glycated hemoglobin with high sensitivity and the glycated hemoglobin must be suitably modified to be recognized by the antibody. Moreover, since it is difficult to form an antigen-antibody complex, a turbidity test performed by reacting a polyhapten consisting of several antigenic determinants and measuring a result of the reaction, is required.

However, according to an exemplary embodiment, glycated hemoglobin may be easily detected by binding a hydroxyl group of a cis-diol to a boronate moiety, both of which are present in the glycated hemoglobin, without modification of the glycated hemoglobin and without using a specific antibody for the glycated hemoglobin, which requires extensive development efforts. The glycated hemoglobin is HbA1c wherein a glucose is covalently bonded to a valine-terminal amine in β-chain and cis-diols exist on two β-chains, respectively. That is, a cis-diol in the glycated hemoglobin is bonded to a boronate moiety in the second material (d) to allow the glycated hemoglobin to be fixed inside the second detection chamber 140.

The first detection chamber 130 and the second detection chamber 140 may have fixing regions (a) to which the first material (b) and the second material (d) are fixed, respectively. The fixing region (a) may be an inner surface of the detection chamber without particular limitation thereto. The fixing region (a) may include a silicon wafer, glass, quartz or plastic. The fixing region (a) may also include gold, silver, platinum, aluminum or copper. The fixing region (a) may include a silicon wafer, glass, quartz or plastics and a top side thereof may be further coated with gold, silver, platinum, aluminum or copper.

The first material (b) and the second material (d) may be fixed to the fixing region (a) by any conventional method such as a physical or electrochemical process. For instance, vacuum filtration, self-assembly, a Lanmuir-Blodgett method, solution casting, bar coating, dip coating, spin coating, injection coating, roll-to-roll, or the like, may be used to place and fix the first material (b) and the second material (d) to the fixing regions of respective detection chambers, without being particularly limited thereto.

The first detection chamber 130 may be connected to the sample chamber 110 and the reagent chamber 120 via channels and, in order to control a flow of the fluid, the valve may be any one selected from different types of microfluidic valves. For instance, the valve may be a normally closed valve, as described above. The second detection chamber 140 may be connected to the first detection chamber 130 via a channel.

In addition to the sample chamber 110, reagent chamber 120 and first and second detection chambers 130 and 140, the microfluidic structure 170 may further include a washing buffer chamber 150 in which a washing buffer is contained to wash away residue remaining after the reaction in the first and second detection chambers 130 and 140, and a waste chamber 160 in which the discarded impurities and the residue after washing using the washing buffer are received.

The washing buffer chamber 150 is connected to the first detection chamber 130 or the second detection chamber 140 via a channel and, in order to control a flow of the fluid, the channel may have a valve mounted thereon. The valve may be a normally closed valve as described above.

The waste chamber 160 is connected to the first and second detection chambers 130 and 140 via channels and, in order to control a flow of the fluid, the channel may have a valve mounted thereon. The valve be a normally closed valve to close the channel to prevent the fluid from flowing until a predetermined external power is applied to the valve and the valve opens the channel, or a normally open valve to open the channel and allow the fluid to flow before a predetermined external power is applied to the valve and the valve closes the channel, wherein these valves are mounted on the channels at the outlet side of each of the first and second detection chambers, in sequential order, thereby more accurately controlling the fluid flow.

The valve mounted on the channel to control the fluid flow may be formed using a mixture of a phase transition material and a heating fluid. The phase transition material may be wax, gel or a thermoplastic resin. The wax may be a paraffin wax. The gel may be selected from polyacrylamide, polyacrylate, polymethacrylate or polyvinylamide. The thermoplastic resin may be selected from, for example, cyclic olefin copolymer (COC), polymethylmethacrylate (PMMA), polycarbonate (PC), polystyrene (PS), polyoxymethylene (POM), perfluoralkoxy (PFA), polyvinylchloride (PVC), polypropylene (PP), polyethylene terephthalate (PET), polyetheretherketone (PEEK), polyamide (PA), polysulfone (PSU) or polyvinylidene fluoride (PVDF). The heating fluid may include a hydrophobic carrier oil and a number of micro-heating particles dispersed in the carrier oil. The micro-heating particle may have a diameter ranging from several tens to several hundred nanometers (nm). The micro-heating particle shows a rapid increase in temperature when energy is supplied by, for example, laser-beam irradiation, thus being heated. The micro-heating particle may be a microfine metal oxide particle having ferromagnetic properties.

The microfluidic device 200 according to an exemplary embodiment may further include an external energy source 195 to supply energy to the valve, for example, a laser. The laser may have a laser diode (LD) irradiating a laser beam to a solidified valve. When the solidified valve is irradiated by the laser beam of the laser source, the valve is fused to be flowable by the external energy from the laser beam, and then, rapidly expands to control opening and closing of a channel.

A detection unit 210 may be provided outside the microfluidic structure 170 and may measure an intensity of light generated through chemical luminescence in the first and second detection chambers 130 and 140. The detection unit 210 may have a light receiving part to receive light generated through chemical luminescence and an analysis part to analyze the light intensity received by the light receiving part and calculate a concentration of an analyte based on the analyzed result.

The light receiving part generates electrical signals according to an intensity of incident light and may include, for example, a depletion layer photodiode, avalanche photodiode (APD), photomultiplier tube (PMT), etc.

The analysis part may calculate the concentration of the analyte contained in the detection chamber from the light intensity received by the light receiving part, using a predetermined standard curve.

Figure 4:
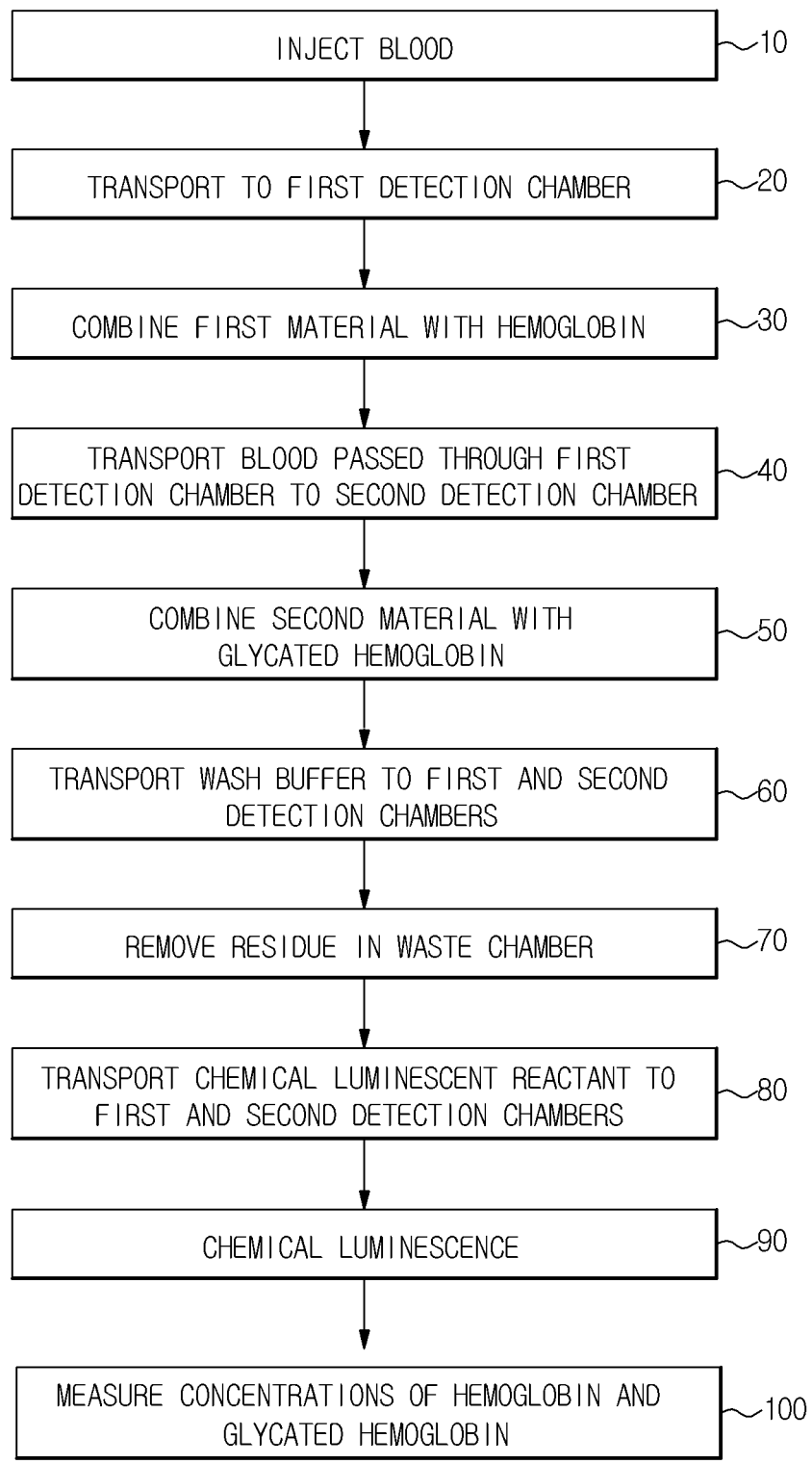
FIG. 4 is a flowchart showing a method of detecting hemoglobin using a microfluidic device according to an exemplary embodiment.

FIG. 4 is a flowchart illustrating a method for detection of hemoglobin using the foregoing microfluidic device according to an exemplary embodiment.

For example, whole blood extracted from a test subject is injected into the sample chamber 110 (operation 10), and transported into the first detection chamber 130 by opening a closed valve of a channel that connects the sample chamber 110 and the first detection chamber 130 and using centrifugal force generated by rotating the platform 180 as a driving pressure (operation 20).

When the whole blood is fed from the sample chamber 110 to the first detection chamber 130, the first material (b) fixed in the first chamber 130 combines with the hemoglobin (c) in the blood (operation 30). The first material (b) is a material that binds to hemoglobin (c) which is a positive colloid, and contains a positively charged material. The positively charged material may have an amine group or a polyamine group. The first material (b) is fixed to a fixing region (a) inside the first detection chamber 130 and may be attached to the fixing region (a) without a specific alignment. The first material (b) may be fixed to the fixing region (a) by any conventional method such as a chemical, physical or physicochemical method. For instance, vacuum filtration, self-assembly, a Lanmuir-Blodgett method, solution casting, bar coating, dip coating, spin coating, injection coating, roll-to-roll, or the like, may be used to place and fix the first material (b) inside the first detection chamber 130, without being particularly limited thereto.

The amine group or polyamine group in the first material (b) binds to the hemoglobin (c), thereby enabling the hemoglobin (c) to be fixed in the first detection chamber 130. In this regard, the platform 180 may be shaken by alternately rotating the platform 180 several times in right and left directions, thereby more effectively combining the first material (b) with the hemoglobin (c).

After passing through the first detection chamber 130, the blood is transported into the second detection chamber 140 using centrifugal force as a driving pressure (operation 40). Following this, a second material (d) fixed in the second detection chamber 140 is specifically combined with glycated hemoglobin (e) in the blood (operation 50). The second material (d) is a material binding to a hydroxyl group of a cis-diol contained in the glycated hemoglobin (e), and contains a boronate moiety. The boronate moiety may be selected from a group consisting of boric acid, boronate compounds and phenylboronic acid. For example, the second material (d) having the boronate moiety may be 4-carboxyphenylboronic acid, 3-nitro-5-carboxyphenylboronic acid, m-aminophenylboronic acid, 4-mercaptophenylboronic acid, thiophene-3-boronic acid and a phenylboronic acid terminated alkane thiol, without being particularly limited thereto. The second material (d) is fixed to another fixing region (a) inside the second detection chamber 140 and may be fixed to the fixing region (a) without specific alignment or arrangement. Like the foregoing first material (b), the second material (d) may be fixed to the fixing region (a) inside the second detection chamber 140 by any conventional method such as a chemical, physical or physicochemical method.

A boronate moiety (HO-B-OH) of the foregoing second material (d) binds to a cis-diol contained in the glycated hemoglobin (e), thereby enabling the glycated hemoglobin (e) to be fixed in the second detection chamber 140. In this case, the platform 180 may be shaken several times in right and left directions, thereby more effectively combining the second material (d) with the glycated hemoglobin (e).

When the hemoglobin (c) and the glycated hemoglobin (e) are combined with the first material (b) and the second material (d) in the first and second detection chambers, respectively, and are fixed to the fixing region (a) of each of the chambers, the closed valve mounted on the channel that connects the washing buffer chamber 150 with the first detection chamber 130 is opened and the washing buffer is introduced into the first detection chamber 130 and the second detection chamber 140 using centrifugal force as a driving pressure (operation 60).

After feeding the washing buffer into the first and second detection chambers, the closed valve mounted on the channel that connects the first and second detection chambers with the waste chamber 160 is opened and uncombined residue is transported into the waste chamber 160 by the washing buffer, and is then removed (operation 70). After transporting the uncombined residue into the waste chamber 160 and removing the same, the opened valve is closed to prevent a chemically luminescent reactant fed into the first and second detection chambers from flowing toward the waste chamber 160.

After removing the uncombined residue from the detection chamber, the closed valve mounted on the channel that connects the reagent chamber 120 with the first detection chamber 130 is opened, and the chemically luminescent reactant is transported into the first detection chamber 130 and the second detection chamber 140 using centrifugal force as a driving pressure (operation 80). The chemically luminescent reactant may contain the foregoing luminescent material and the oxidant and, for example, luminol as the luminescent material and $H_2O_2$ as the oxidant.

Luminol and $H_2O_2$ may undergo chemical luminescence catalyzed by Fe, a transition metal contained in hemoglobin (operation 90).

The detection unit 210 may measure an intensity of light generated through chemical luminescence in the first and second chambers 130 and 140, and detect a concentration of each of hemoglobin and glycated hemoglobin (operation 100). The light receiving part of the detection unit 210 may measure the intensity of light generated through chemical luminescence in the detection chamber, and the analysis part may detect a concentration of the glycated hemoglobin from the light intensity measured by the light receiving part, using a pre-determined standard curve which shows an intensity of chemical luminescence in relation to the concentration of the glycated hemoglobin.

Figure 5:
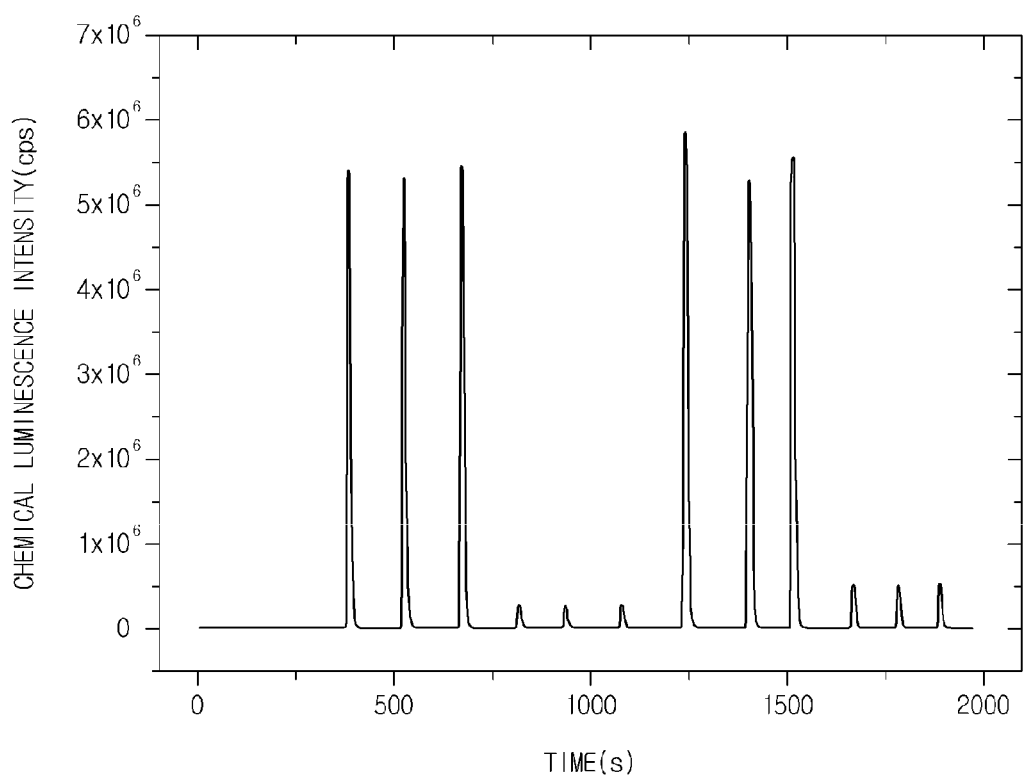
FIG. 5 is a graph illustrating an intensity of chemical luminescence measured using a microfluidic device according to an exemplary embodiment.

FIG. 5 is a graph illustrating the intensity of chemical luminescence measured by the microfluidic device according to an exemplary embodiment.

Referring to FIG. 5, intensities of chemical luminescence of total hemoglobin in blood containing 5% glycated hemoglobin (three higher peaks among six peaks at the left side of the graph) and intensities of chemical luminescence of the glycated hemoglobin (three lower peaks among six peaks at the left side of the graph) were measured three times, respectively. On the other hand, intensities of chemical luminescence of total hemoglobin in blood containing 10% glycated hemoglobin (three higher peaks among six peaks at the right side of the graph) and intensities of chemical luminescence of the glycated hemoglobin (three lower peaks among six peaks at the right side of the graph) were also measured three times, respectively.

Measured values are shown in TABLE 1 below.

TABLE 1

| Chemical luminescence intensity of total hemoglobin (cps) | Chemical luminescence intensity of glycated hemoglobin (cps) | Ratio of glycated hemoglobin (%) |
| --- | --- | --- |
| $5.41454 \times 10^6$ | 298662 | 5.51593 |
| $5.32151 \times 10^6$ | 279228 | 5.24716 |
| $5.46848 \times 10^6$ | 282428 | 5.16465 |
| $5.85759 \times 10^6$ | 515508 | 8.80068 |
| $5.2923 \times 10^6$ | 510786 | 9.65149 |
| $5.56381 \times 10^6$ | 538286 | 9.67477 |

In TABLE 1, the three columns at the left side denote measured results of the blood containing 5% glycated hemoglobin, while the three columns at the right side denote measured results of the blood containing 10% glycated hemoglobin.

Referring to the three columns at the left side in TABLE 1, it can be seen that ratios (third column) of the intensities of chemical luminescence of the glycated hemoglobin (second column) to the intensities of chemical luminescence of the total hemoglobin in the blood containing 5% glycated hemoglobin (first column) are very close to an actual concentration of the glycated hemoglobin (5%).

Referring to the three columns at the right side in TABLE 1, it can also be seen that ratios (sixth column) of the intensities of chemical luminescence of the glycated hemoglobin (fifth column) to the intensities of chemical luminescence of the total hemoglobin in the blood containing 10% glycated hemoglobin (fourth column) are very close to an actual concentration of the glycated hemoglobin (10%).

Figure 6:
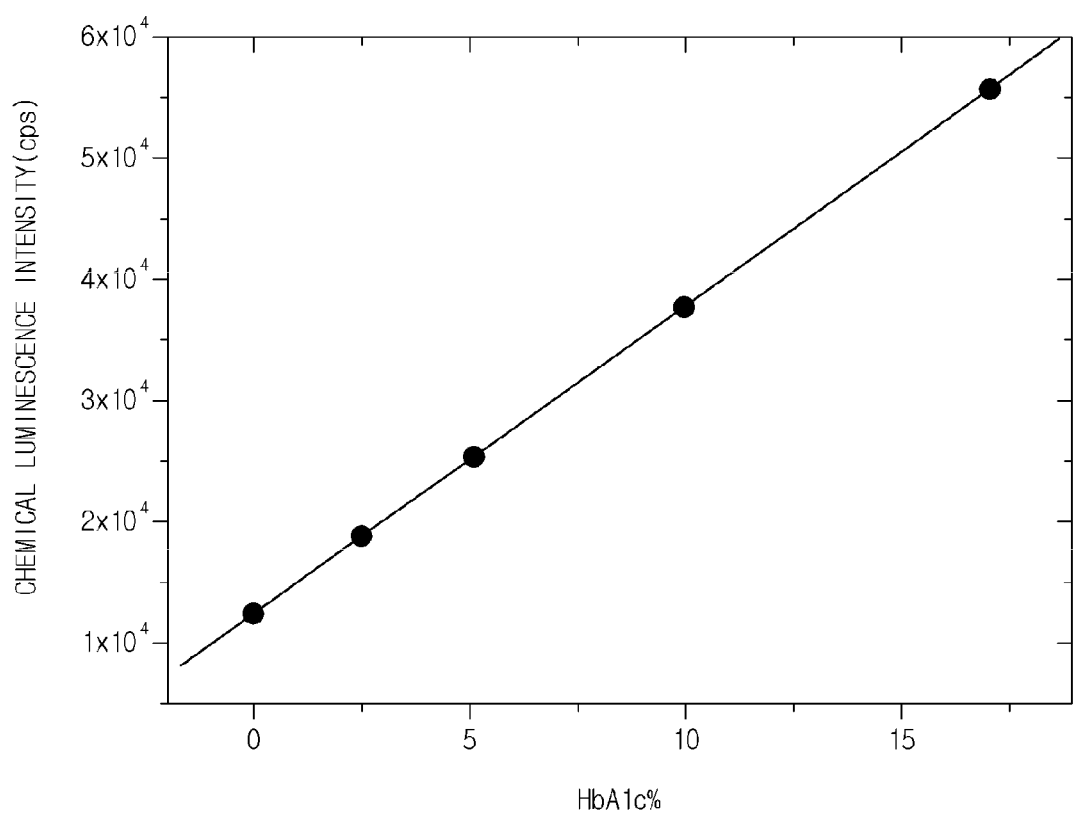
FIG. 6 is a standard curve showing a concentration of glycated hemoglobin and an intensity of chemical luminescence in relation to the same according to an exemplary embodiment.

FIG. 6 is a standard curve showing a concentration of glycated hemoglobin and an intensity of chemical luminescence in relation to the same according to an exemplary embodiment.

As such, the standard curve may be prepared in advance by plotting intensities of chemical luminescence in relation to different concentrations of glycated hemoglobin. For instance, when concentrations of glycated hemoglobin are 0%, 2.5%, 5%, 10% and 17%, respectively, intensities of chemical luminescence according to concentration may be plotted, thus obtaining the standard curve shown in FIG. 6. After measuring an intensity of light generated through chemical luminescence in the detection chamber using the light receiving part of the detection unit 210, the analysis part may calculate the concentration of glycated hemoglobin from the measured light intensity by applying the standard curve shown in FIG. 6.

By measuring the intensity of light generated through chemical luminescence in the first detection chamber 130, the total hemoglobin concentration may be detected. Subsequently, by measuring the intensity of light generated through chemical luminescence in the second detection chamber 140, the concentration of the glycated hemoglobin may be detected. Consequently, concentrations of hemoglobin and glycated hemoglobin may be simultaneously detected by the microfluidic structure 170, which in turn enables calculation of percent (%) concentration of the glycated hemoglobin relative to the total hemoglobin.

According to one or more exemplary embodiments, glycated hemoglobin may be selectively detected by binding a boronate moiety to a cis-diol molecule, without using a material difficult to handle or manage, such as a biomaterial, for example, antigen, in order to selectively detect the glycated hemoglobin.

Moreover, by detecting hemoglobin through chemical luminescence, an alternative labeling process to detect hemoglobin may be omitted, thereby enabling size reduction of a measurement apparatus and decreasing production costs.

Furthermore, simultaneous detection of hemoglobin and glycated hemoglobin may be executed in a single microfluidic structure, thereby measuring a content ratio of glycated hemoglobin in total hemoglobin.

Although exemplary embodiments have been described above with the accompanying drawings, it is clearly understood that these exemplary embodiments do not particularly restrict the scope. Accordingly, it would be appreciated by those skilled in the art that various substitutions, variations and/or modifications may be made in these exemplary embodiments without departing from the principles and spirit of the inventive concept. Therefore, it is understood that the inventive concept is not restricted to technical configurations and arrangements illustrated above.

What is claimed is:

1. A microfluidic structure comprising:
    a sample chamber which receives and accommodates blood;
    a reagent chamber which contains a luminescent reactant;
    a first detection chamber which contains a first material that is positively charged;
    a second detection chamber which is connected to the first detection chamber, and contains a second material having a boronate moiety; and
    at least one channel which connects the sample chamber, the reagent chamber and the first and second detection chambers.

2. The microfluidic structure according to claim 1, wherein the luminescent reactant comprises a luminescent material and an oxidant.

3. The microfluidic structure according to claim 2, wherein the luminescent material is at least one selected from a group consisting of luminol, ucigenin, 7-(4,6-dichloro-1,3,5-triazinylamino)-4-methylcoumarin (DTMC), pyrene, perylene, p-quarterphenyl, 1,6-diphenyl-1,3,5-hexatriene, 1,3-cyclohexanedione, 1,4-bis(5-phenyloxazol)benzene, bis(2,4-dimethylpentadienyl)ruthenium, 1-ethylnaphthalene, 1-pyrenedodecanoic acid, 2,3-naphthalenedicarboxaldehyde, 2-aminoacridone, 3-phenylubelliferone 3,3'-diethylthiadicarbocyanine iodide, 4-hydroxybenzhydrazide, 6-aminofluorescein, 7-ethoxy-4-methylcoumarin and 7-methoxycoumarin.

4. The microfluidic structure according to claim 1, wherein the first material contained in the first detection chamber has an amine group or a polyamine group.

5. The microfluidic structure according to claim 4, wherein the first detection chamber comprises a fixing region to which the first material is fixed.

6. The microfluidic structure according to claim 5, wherein the fixing region of the first detection chamber is formed using a silicon wafer, glass, quartz, metal or plastic.

7. The microfluidic structure according to claim 6, wherein the fixing region of the first detection chamber comprises gold, silver, platinum, aluminum or copper.

8. The microfluidic structure according to claim 1, wherein the boronate moiety is selected from a group consisting of boric acid, boronate compounds and phenylboronic acid.

9. The microfluidic structure according to claim 8, wherein the second detection chamber comprises a fixing region to which the second material containing the boronate moiety is fixed.

10. The microfluidic structure according to claim 9, wherein the fixing region of the second detection chamber is formed using a silicon wafer, glass, quartz, metal or plastic.

11. The microfluidic structure according to claim 10, wherein the fixing region of the second detection chamber comprises gold, silver, platinum, aluminum or copper.

12. The microfluidic structure according to claim 1, further comprising at least one valve which controls fluid transportation in the at least one channel which connects the sample chamber, the reagent chamber and the first and second detection chambers.

13. The microfluidic structure according to claim 12, wherein the at least one valve comprises a mixture of a phase transition material and a heating fluid.

14. The microfluidic structure according to claim 13, wherein the phase transition material is at least one selected from a group consisting of waxes, gels and thermoplastic resins.

15. The microfluidic structure according to claim 13, wherein the heating fluid includes a carrier oil and a number of micro-heating particles dispersed in the carrier oil, and the micro-heating particles are micro-metal oxide particles.

16. A microfluidic device comprising:
    a platform comprising the microfluidic structure according to claim 12;
    a detection unit which detects light generated by chemical luminescence of the luminescent reactant; and
    an external energy source which supplies energy to the valve, wherein a fluid contained in the microfluidic structure is transported using centrifugal force generated by rotation of the platform.

17. The microfluidic device according to claim 16, wherein the external energy source is a laser beam source.

18. The microfluidic device according to claim 16, wherein the detection unit measures an intensity of light generated through chemical luminescence in the first and second detection chambers.

19. A method of measuring hemoglobin using a microfluidic device, the method comprising:
    injecting blood into a sample chamber of the microfluidic device;

transporting the blood from the sample chamber into a first detection chamber of the microfluidic device and combining hemoglobin contained in the blood with a first material that is positively charged fixed inside the first detection chamber;

transporting the blood from the first detection chamber into a second detection chamber and combining glycated hemoglobin contained in the blood with a second material having a boronate moiety fixed inside the second detection chamber;

transporting a luminescent reactant received in a reagent chamber of the microfluidic device into the first and second detection chambers to induce chemical luminescence;

detecting light generated through chemical luminescence in the first and second detection chambers; and measuring hemoglobin based on the detected light.

20. The method according to claim 19, wherein the measuring the hemoglobin based on the detected light comprises measuring hemoglobin in the blood based on the detected light generated through chemical luminescence in the first detection chamber and measuring glycated hemoglobin in the blood based on the detected light generated through chemical luminescence in the second detection chamber.

* * * * *